United States Patent [19]

Hughes

[11] Patent Number: 5,280,291
[45] Date of Patent: Jan. 18, 1994

[54] THERMODYNAMICS-BASED SIGNAL RECEIVER

[75] Inventor: Michael S. Hughes, Ames, Iowa

[73] Assignee: Iowa State University Research Foundation, Inc., Ames, Iowa

[21] Appl. No.: 963,134

[22] Filed: Oct. 19, 1992

[51] Int. Cl.$^5$ .............................................. G01S 3/02
[52] U.S. Cl. ..................... 342/351; 342/195
[58] Field of Search ............... 342/25, 196, 351, 195

[56] References Cited

U.S. PATENT DOCUMENTS

| | | | |
|---|---|---|---|
| 4,841,490 | 6/1989 | Carron | 367/38 |
| 5,068,597 | 11/1991 | Silverstein et al. | 312/192 X |
| 5,103,427 | 4/1992 | Erdol et al. | 367/7 |
| 5,164,730 | 11/1992 | Jain | 342/25 |

OTHER PUBLICATIONS

Q. T. Zhang, "An Entropy-Based Receiver for the Detection of Random Signals & Its Application to Radar", *Signal Processing* 18 (1989) 387–396 Elsevier Science Publishers B.V.

Patent Application 07/906,571 for "Entropy-Based Signal Receiver" by Michael S. Hughes, Filed Jun. 30, 1992.

*Primary Examiner*—Mark Hellner
*Attorney, Agent, or Firm*—Robert E. Malm

[57] ABSTRACT

The thermodynamics-based signal receiver transforms contiguous segments of a received signal into thermodynamics-related quantities using an analog of a statistical-mechanics-related quantities using an analog of a statistical-mechanics expression for a thermodynamic variable and uses these thermodynamics-related quantities as the means to measure changes in the signal as a function of time or origin. The changes that are of interest are those associated with either signal level or signal structure. Signal-processing analogs of statistical mechanics expressions for thermodynamic variables are measures that respond in some fashion to either type of change. By comparing thermodynamics-related transformations of received signals, one can obtain information about the emitters of the received signals and the nature of the medium through which the signals were propagated. The sensitivity of the thermodynamics-based receiver is significantly better than the more conventional signal energy-based receiver in detecting the changes in a signal that result from reflection or scattering by inhomogeneities in a wave-propagating medium.

37 Claims, 2 Drawing Sheets

1

THERMODYNAMICS-BASED SIGNAL RECEIVER

BACKGROUND OF INVENTION

This invention relates generally to receivers of electrical signals in apparatus such as radar and sonar wherein electromagnetic or acoustic waves are used to "probe" an environment of uncertain composition and the resulting scattered waves from the environment are analyzed for the purpose of determining the nature of the environment. More particularly, the invention relates to the processing methods practices by the signal processors in such receivers.

The use of probing signals for the identification of objects, inhomogeneities, or disturbances in a wave-propagation-supporting medium has been a basic environmental investigative technique for centuries. However, only since the middle of the twentieth century has the knowledge of signal detection principles and the capability of implementing complicated signal processing designs in hardware resulted in sophisticated signal processors that test the theoretical limits to signal detection and analysis.

The genesis of radar and sonar signal processors were the simple but effective square-law detector and its close relative, the envelope detector, that were used in the detection of radar and sonar pulses in the World War II era. It was subsequently discovered that the so-called correlation processor, which computed the correlation of received signals with replicas of the transmitted signal, was theoretically more effective in extracting the returning signals from the everpresent background noise and interference. Interestingly, the envelope detector can be a very good approximation to the correlation processor when the transmitted signal is a simple pulse and the parameters of the envelope detector are properly chosen.

The square-law detector, the envelope detector, and the correlation detector all share one attribute—they all calculate a quantity proportional to the energy of the received signal. In the case of received signals that are replicas of the transmitted signal, obtained, for example, by reflection from a plane surface, the use of an energy measure as the means of detection is well-supported by theory which shows that with such measures, the highest possible signal-to-noise ratio is obtained. However, there is no reason to believe that energy-measure processors are the most effective detectors of received signals that result from reflection or scattering of the transmitted wave by more complicated media structures and compositions. In such situations one is looking for changes in received signals as a function of time and direction of arrival and not whether a delayed and attenuated version of the transmitted signal is being received. In these circumstances, certain experimental results suggest that measures based on thermodynamic analogs are significantly more effective than energy measures as a means of detecting such complicated returning signals.

BRIEF SUMMARY OF INVENTION

The thermodynamics-based signal receiver transforms a received signal into an analog of a thermodynamic variable, or a quantity that is closely related to such a thermodynamic analog, and uses this thermodynamic analog as the means to measure changes in the signal as a function of time or origin. The changes that are of interest are those associated with either signal level or signal structure. The thermodynamic analogs are measures that respond in some fashion to either type of change.

The thermodynamics-based signal receiver transforms time segments of a received signal into thermodynamics-related quantities. By comparing thermodynamics-related transforms of received signals, one can obtain information about the emitters of the received signals and the nature of the medium through which the signals are propagated. The sensitivity of the thermodynamics-based receiver is significantly better than the more conventional signal energy-based receiver in detecting the changes in a signal that result from reflection or scattering by inhomogeneities in a wave-propagating medium.

The thermodynamics-based signal receiver in combination with an infrared radiation lens and detector can be used to monitor the temperatures of devices on an integrated circuit chip by scanning the chip and obtaining a thermodynamics-related measure of the infrared radiation emitted by the devices. This type of signal receiver is also appropriate for imaging radars operating at millimeter and shorter wavelengths where one is interested in determining the shape and contours of a reflecting object. The present invention can also be used in ultrasonic acoustic probing systems used for medical diagnostics and nondestructive testing of manufactured items. In such systems, the test object is irradiated with a narrow beam of ultrasonic acoustic waves. Any discontinuities or inhomogeneities will cause portions of the incident acoustic waves to be scattered. By transforming these scattered signals into thermodynamics-related quantities, the thermodynamics-based signal receiver permits the shapes and contours of regions of different densities, that are concealed within the subject, to be visualized with greater sensitivity than has hitherto been possible.

DESCRIPTION OF THE PREFERRED EMBODIMENT

Figure 1:
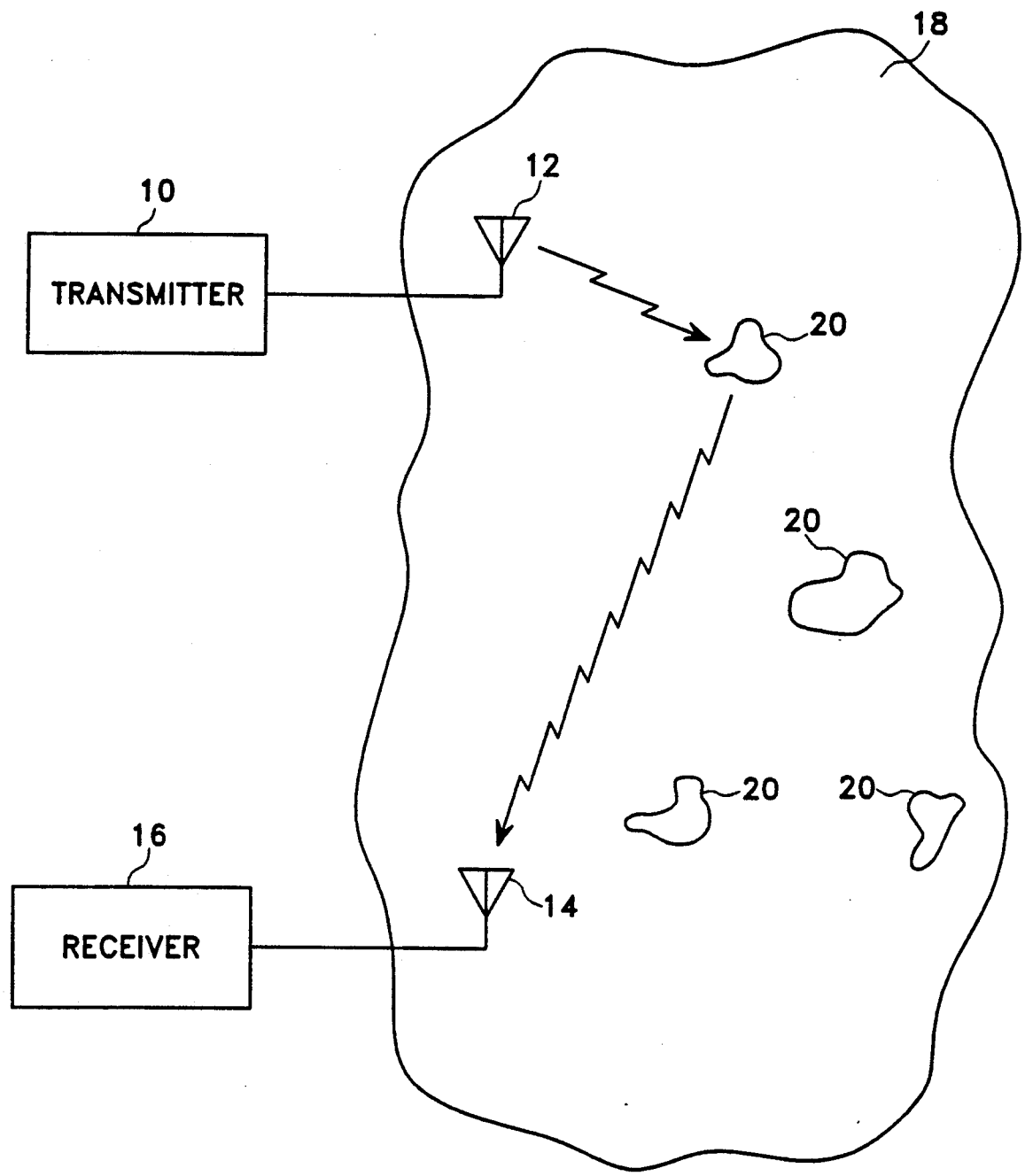
FIG. 1 shows a generic version of a probing system for characterizing an environment by means of the waves reflected or scattered by inhomogeneities.

For the purposes of this discussion, a system for characterizing an environment by means of waves reflected or scattered by inhomogeneities of any type will be called a probing system. A generic version of a probing system is shown in FIG. 1. It is comprised of (1) a transmitter 10 which generates electrical signals, (2) a wave-generating means 12 which converts the electrical signals into waves (e.g. an antenna in the case of radio-frequency electromagnetic (R-F- EM) waves, a modulatable light source and reflector or lens in the case of optical-frequency electromagnetic (O-F EM) waves, or a transducer in the case of acoustic waves); (3) a wave-converting means 14 which converts received waves into electrical signals (e.g. an antenna (R-F EM waves), a reflector or lens and a light detector (O-F EM waves), or a transducer (acoustic waves)); a (4) a receiver 16 that transforms the received electrical signals into measures from which the structural or compositional characteristics of the environment in which the probing system operates can be deduced.

The operating premise of the system is that the wave-generating means 12 and the wave-converting means 14 are coupled together by the wave-propagating medium 18 and that the received waves that result from reflection or scattering from inhomogeneities 20 will be affected by the character of the inhomogeneities.

The wave-generating means 12 and the wave-converting means 14 may be individual devices or arrays of devices. They may be highly-directive in their radiation patterns or omnidirectional. They may be co-located or spaced apart as shown in the figure. With the proper choice of transmitted signals, the wave-generating means and the wave-converting means may be a single device.

Figure 2:
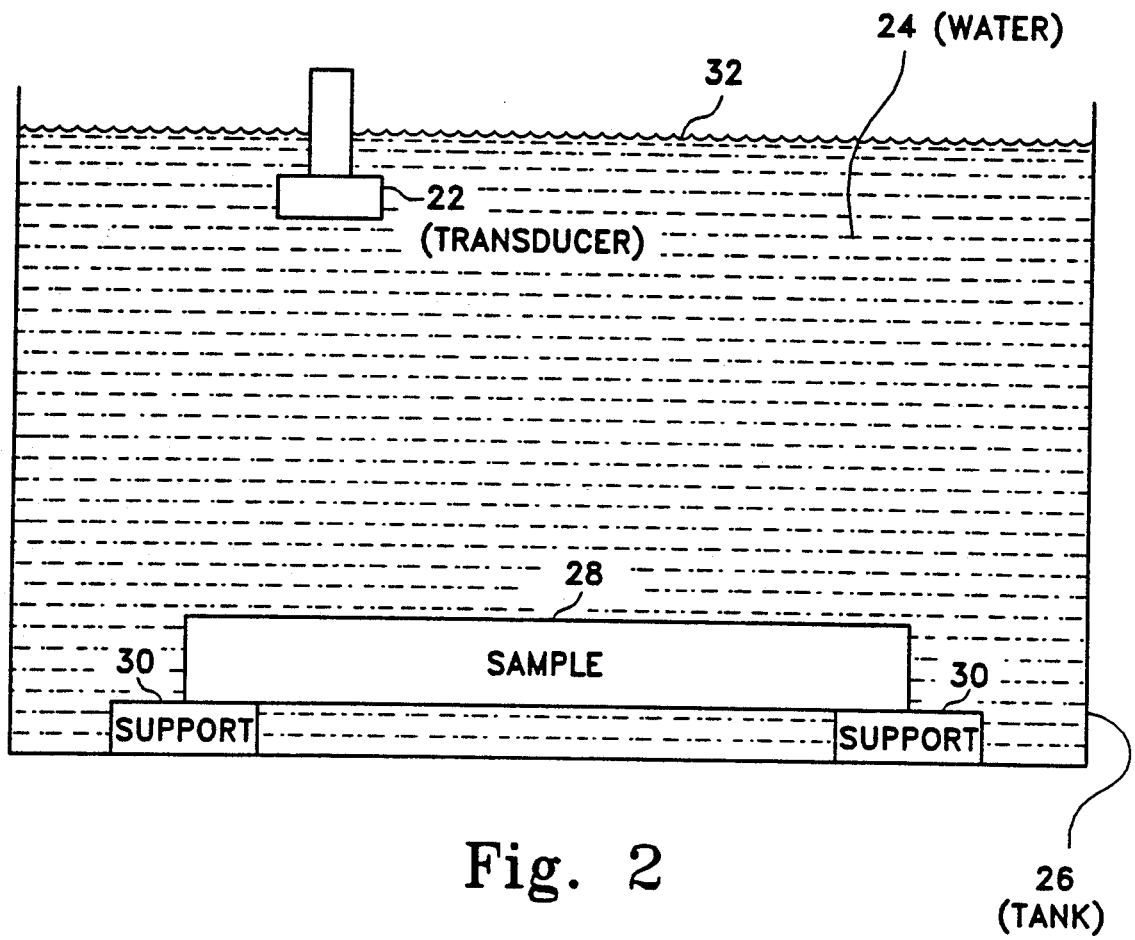
FIG. 2 illustrates a probing system for detecting and characterizing discontinuities and inhomogeneities within a test object by means of ultrasonic acoustic irradiation of the test object.

For example, the arrangement for a non-destructive testing application might be as shown in FIG. 2. The functions of the wave-generating means 12 and the wave-converting means 14 are performed by the single narrow-beam acoustic transducer 22 having a downward-pointing beam. The transducer is immersed in water 24 contained in tank 26. The sample to be non-destructively tested 28 rests on supports 30 near the bottom of the tank. A three-dimensional determination of voids in the sample is obtained by (1) pulsing the transducer and analyzing the signal returns as a function of round-trip propagation time and (2) raster-scanning the transducer in a plane parallel to the water surface 32.

Figure 3:
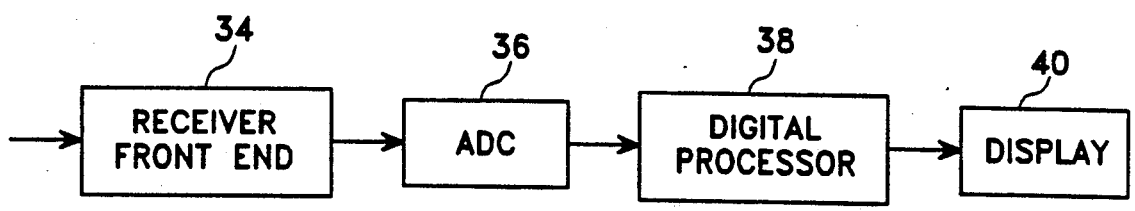
FIG. 3 shows the functional block diagram of the thermodynamics-based signal receiver.

The functional block diagram of the receiver 16 (FIG. 1) is shown in FIG. 3. The receiver is comprised of a front end 34 which amplifies the received signals and translates the amplified signals to baseband (i.e. a frequency band extending from zero frequency to some higher value) if the transmitted signals are not already at baseband.

The translating means can be a simple envelope detector if the transmitted signals are amplitude-modulated sinusoids. If the transmitted signals are phase- or frequency-modulated sinusoids, then the translating means can be implemented with two mixer-lowpass filter combinations—one combination for generating the inphase baseband component and the other for generating the quadrature baseband. The inphase combination functions by forming the product of the received signals and a cosine-function signal at the nominal center frequency of the transmitted signals and removing the upper sidebands from the product signal by means of the lowpass filter. Similarly, the quadrature combination functions by performing the same operations with a sine-function signal substituted for the cosine-function signal.

It will be assumed in the material that follows that both inphase and quadrature baseband signals are produced at the output port of the receiver front end 34. A single-baseband signal output from the receiver front end will be recognized as a special case of the more general two-signal case.

The two baseband signals from the receiver front end 34 are independently sampled and digitized at time intervals of $\chi$ by the p-bit analog-to-digital (A/D) converter 36 where the reciprocal of $\chi$ is equal to or greater than the Nyquist rate and p is an integer typically equal to or greater than 8. The two p-bit word sequences from the A/D converter enter the digital processor 38 which optionally may combine the two word streams into a single word stream by selecting the larger of corresponding words in the two word sequences, by summing the absolute values of corresponding words in the two word sequences, or by summing the squares of the values of corresponding words in the two word sequences and extracting the square root of the result. Persons skilled in the art will recognize other possibilities for combining two word sequences into a single word sequence while at the same time conserving the essential information content of both word sequences.

It may be desirable in some situations to perform repeated scans and average the data so that more consistent and reliable results can be obtained. In order to accommodate the increased precision of averaged data, the word lengths utilized in the digital processor 38, denoted by q in the material that follows, should be greater than p.

It will be assumed for simplicity that subsequent processing by the digital processor 38 involves a single word sequence $f_s$ where m is an integer that identifies the sequence of the samples in time. If the two original sequences are not combined into a single sequence, then the processing described below is performed on each of the sequences.

The digital processor 38 divides the word sequence into groups of M words. The groups may overlap if abrupt changes in successive outputs of the digital processor are to be minimized. For each M-word group the digital processor generates a "thermodynamics-related" number, the output of the digital processor being a signal-processing analog of a thermodynamics variable.

A thermodynamics-related number is the value of a statistical mechanics expression for a thermodynamic variable that is obtained by equating the probability of the occurrence of a particular signal level in a received signal segment to the probability of finding a thermodynamic system in an equilibrium state corresponding to a particular energy eigenvalue at some specified temperature. The thermodynamics-related numbers may be obtained by using the exact statistical-mechanics expression for a thermodynamic variable or by using an expression that is a function of the thermodynamic variable.

The thermodynamics-related output from the digital processor 38 can be used to detect and characterize departures from homogeneity in the test environment. The rationale for transforming the input signal segments into thermodynamics-related quantities rather than energies (as is commonly done) becomes apparent when one considers the scattered signals that result when an inhomogeneity in the wave-propagating medium is illuminated with a pulsed waveform. The scattered wave is a summation of attenuated and delayed versions of the incident pulsed waveform resulting in a signal structure that typically appears to be considerably different from the incident waveform. The same is true of incident signals other than pulsed waveforms. The utilization of the energy of the scattered waveform as a means of characterizing the inhomogeneity is a one-dimensional attempt that obviously does not fully use all of the information contained in the scattered waveform. Two homogeneities might scatter the same amount of energy and yet might have completely different effects on the structure of the scattered signal. Signal-processing analogs of thermodynamic variables, on the other hand, are statistical characterizations of the scattered signal and are affected by both the signal energy and the signal structure. Thus, a thermodynamics-related measure of the scattered signal permits more sophisticated deductions to be made about the nature of the inhomogeneities that cause the scattering to occur.

The thermodynamics-related numbers from the digital processor 38 are supplied to the display 40 where they are displayed in accordance with a user's needs. In the non-destructive testing case illustrated in FIG. 2, for example, for a fixed position of the transducer 22, the thermodynamics-related numbers may be plotted as ordinates against propagation times as abscissas in a Cartesian coordinate system.

For a one-dimensional scan of the transducer 22, the thermodynamics-related numbers may be plotted as spots of different shades of gray in a Cartesian coordinate system, the transducer position being the abscissa and the propagation time being the ordinate of a spot.

For a two-dimensional scan of the transducer, the thermodynamics-related numbers may be plotted as spots of different shades of gray in a Cartesian coordinate system, the two coordinates of the transducer position corresponding to the ordinate and abscissa of a spot. In this case, the thermodynamics-related numbers are restricted to a particular propagation time.

Four examples of thermodynamic variables from which analogs can be derived for signal analysis purposes are sum-over-states Z, entropy H, energy E, and specific heat capacity at constant volume $C_V$ which are given by R. C. Tolman, *THE PRINCIPLES OF STATISTICAL MECHANICS*, 1st ed., Oxford University Press, London, 1955, p. 567 as:

$$H = -\mu \frac{\partial}{\partial \mu} \log Z(\mu) + \log Z(\mu) \quad (1)$$

$$E = -\frac{\partial}{\partial \mu} \log Z(\mu) \quad (2)$$

$$C_V = \mu^2 \frac{\partial^2}{\partial \mu^2} \log Z(\mu) \quad (3)$$

where $1/\mu$ has been substituted for the temperature T and constants have been omitted. The sum-over-states quantity $Z(\mu)$ is defined by Tolman on page 532 of his treatise, equation 120.6, by the equation $$Z(\mu) = \sum_{k=1}^{N} \exp(-\mu E_k) \quad (4)$$

where N is the number of different states $k_1$ corresponding to the energy eigenvalues $E_k$.

The thermodynamic energy eigenvalues $E_k$ can be obtained from the probabilities $p(k,\mu_0)$ for finding the thermodynamic system in the different steady states k corresponding to the energy eigenvalues at temperature $\mu_0$ by means of the equation $$E_k = -\frac{\ln p(k,\mu_0)}{\mu_0} \quad (5)$$

which, except for a constant, is Tolman's equation 121.1 on page 533 of his treatise.

Substituting equation (5) in equation (4) we obtain $$Z(\mu) = \sum_{k=1}^{N} p(k,\mu_0)^{\mu/\mu_0} \quad (6)$$

Substituting equation (6) in equations (1), (2), and (3), we obtain, again ignoring constants, expressions for H, E, and $C_V$ in terms of the inverse temperature $\mu$ and the probabilities $p(k,\mu_0)$:

$$H = \left(\frac{\mu}{\mu_0}\right) \frac{\sum_{k=1}^{N} -\ln p(k,\mu_0) p(k,\mu_0)^{\mu/\mu_0}}{\sum_{k=1}^{N} p(k,\mu_0)^{\mu/\mu_0}} + \ln \sum_{k=1}^{N} p(k,\mu_0)^{\mu/\mu_0} \quad (7)$$

$$E = \frac{\sum_{k=1}^{N} \ln[p(k,\mu_0)] p(k,\mu_0)^{(\mu/\mu_0)}}{\mu_0 \sum_{k=1}^{N} p(k,\mu_0)^{(\mu/\mu_0)}} \quad (8)$$

$$C_V = \left(\frac{\mu}{\mu_0}\right)^2 \frac{\sum_{k=1}^{N} p(k,\mu_0)^{\mu/\mu_0} \sum_{k=1}^{N} [\ln p(k,\mu_0)]^2 p(k,\mu_0)^{\mu/\mu_0} - \left(\sum_{k=1}^{N} \ln p(k,\mu_0) p(k,\mu_0)^{\mu/\mu_0}\right)^2}{\sum_{k=1}^{N} p(k,\mu_0)^{\mu/\mu_0}} \quad$$

The signal-processing analogs of the thermodynamic variables are obtained by interpreting the probability $p(k,\mu_0)$ in the expressions above to be the number of occurrences of the magnitude $k\epsilon$ in a group of words divided by the number M of words in the group. The summations over N in the above expressions are interpreted as being over the number $2^q$ of distinct words that can be represented by a q-bit word. The quantity $\epsilon$ is defined by the equation $$\epsilon = \frac{\beta - \alpha}{N} \quad (10)$$

where $\alpha$ and $\beta$ are respectively the lower and upper bounds of the input word sequences $f_=$ which the digital processor 38 transforms into thermodynamics-related outputs.

The signal-processing analogs of thermodynamic variables that result form the signal-level interpretation of the probability $p(k,\mu_0)$ in expressions (6), (7), (8) and (9) include the thermodynamic system inverse temperature $\mu$. In the signal-processing context, $\mu$ becomes a parameter that can be adjusted to secure the best possible signal-processing effectiveness. For example, the detection of foreign objects and inhomogeneities in a propagation medium may be more effectively accomplished by adjusting the inverse temperature parameter in accordance with the particular application and the environmental conditions.

In a recent publication, the inventor described a set of experiments in which he performed a raster scan of a rectangular block of Plexiglas with a pattern of drill holes—artificial "flaws"—in an experimental configuration similar to that shown in FIG. 2. He compared two energy-based receivers with an entropy-based receiver that transformed word groups into entropy by means of equation (6) with $\mu=\mu_0$ and found that the entropy-based receiver was two to three times more sensitive to the presence of small defects in the specimen than the energy-based receivers. (Michael S. Hughes, "A comparison of Shannon entropy versus signal energy for acoustic detection of artificially induced defects in Plexiglas", J. Acoust. Soc. Am 91 (4), Pt. 1, April 1992.)

The signal-processing analogs of thermodynamic sum-over-states, entropy, energy, and specific heat capacity as defined by equations (6), (7), (8), and (9) are four examples of acceptable functional definitions of the processing performed by the digital processor 38 in transforming word groups into thermodynamics-related quantities. As indicated previously, other thermodynamic variables and functions of thermodynamic sum-over-states, entropy, energy, and specific heat capacity and other thermodynamic variables can also be used as signal-processing analogs. Examples of thermodynamics-related functions that are derived from the basic thermodynamic variables are weighted sum-over-states $Z_W$, weighted entropy $H_W$, weighted energy $E_W$, and weighted specific heat capacity $C_{VW}$ as defined by the equations $$Z_w = WZ \quad (11)$$

$$H_w = WH \quad (12)$$

$$E_w = WE \quad (13)$$

$$C_{vw} = WC_v \quad (14)$$

The quantity W in the above expressions is the number of discrete levels in each word group.

If word groups from two word sequences are converted into two sequences of thermodynamics-related numbers, the thermodynamics-related sequences can be combined into a single thermodynamics-related sequence for output to the display 40 by selecting the largest of corresponding numbers in the two thermodynamics-related sequences, summing corresponding numbers, or taking the square root of the sum of the squares of corresponding numbers.

There are obviously many ways for generating thermodynamics-related numbers from input word groups through the manipulation, partition, rearrangement, and approximation of equations that define thermodynamic variables. Any such alternatives that evolve from probability density distribution functions that characterizes the analog received signal segments or the normalized frequency-of-occurrence $p(k,\mu_0)$ of the k'th amplitude level of the digitized received signal segments are within the spirit and scope of the invention.

A thermodynamics-based system for characterizing naturally-occurring signals and the wave-propagating mediums through which they pass is obtained by combining the thermodynamics-based signal receiver with an antenna or transducer, depending on the nature of the waves to be received. A particular configuration that would be useful for monitoring the temperatures of devices on an integrated circuit chip consists of an infrared imaging system—lens and infrared light detector—mounted on a raster-scan assembly of an integrated circuit chip in a raster pattern would result in a display of the thermodynamics-related quantity associated with the infrared radiation produced at each point on the integrated circuit chip. Since the radiation from a point on the chip and the signal-processing analog of the thermodynamic variable is monotonically related to the temperature of the point, the thermodynamics-related quantities are readily translated into temperatures.

A similar system configuration utilizing a visible light imaging system and visible light illumination could be used for detecting and characterizing bubbles, refractive index striae, and other imperfections in optical glass parts.

A thermodynamics-based radar-type probing system is obtained by combining a transmitter, directive transmit and receive antennas, appropriate means to enable the antennas to systematically scan a given region of space, and the thermodynamics-based signal receiver. The intersection of transmit and receive antenna beams determines the region of space from which reflected or scattered waves can be received. A closer specification of the scattering region from which the scattered waves originate is obtained by measuring the propagation time between transmitter and receiver. Such a configuration would permit objects, discontinuities, or other inhomogeneities in the wave-propagating medium to be detected and characterized.

A similar configuration utilizing acoustic waves and transducers to launch and receive them would permit the investigation and characterization of media that does not support electromagnetic propagation but does support the propagation of acoustic waves.

What is claimed is:

1. A signal receiver which detects changes in an electrical signal by transforming a plurality of time segments of said signal into thermodynamics-related quantities by means of a statistical mechanics expression for a thermodynamic variable, or a function thereof, said statistical-mechanics expression being a function of the energy eigenvalue probability function, said energy eigenvalue probability function being the probability of finding a thermodynamic system in an equilibrium state corresponding to a particular energy eigenvalue at some specified temperature as a function of said energy eigenvalue, said thermodynamics-related quantities being obtained by (1) calculating from each signal segment a signal level probability function, said signal level probability function being the probability of occurrence of a particular signal level as a function of signal level, and (2) calculating the value of the statistical mechanics expression, or function thereof, by substituting the signal level probability function for the energy eigenvalue probability function, the differences between said thermodynamics-related quantities being a measure of change among said signal segments.

2. The signal receiver of claim 1 comprising:
   an analog-to-digital converter (ADC) which converts each of said signal segments into at least one sequence of digital words, said word sequences being digital representations of said signal segments;
   a digital processor which transforms said word sequences into said thermodynamics-related quantities.

3. The signal receiver of claim 2 wherein said thermodynamics-related quantities are obtained from a statistical-mechanics expression for the sum-over-states of a thermodynamic system.

4. The signal receiver of claim 1 wherein said thermodynamics-related quantities are obtained from a statistical-mechanics expression for the entropy of a thermodynamic system.

5. The signal receiver of claim 2 wherein said thermodynamics-related quantities are obtained from a statistical-mechanics expression for the energy of a thermodynamic system.

6. The signal receiver of claim 2 wherein said thermodynamics-related quantities are obtained from a statistical-mechanics expression for the specific heat capacity of a thermodynamic system.

7. The signal receiver of claim 2 wherein said thermodynamics-related quantities are obtained from a weighted statistical-mechanics expression for the sum-over-states of a thermodynamic system, the weighting applied to said statistical-mechanics expression being the number of different words associated with each of said signal segments.

8. The signal receiver of claim 2 wherein said thermodynamics-related quantities are obtained from a weighted statistical-mechanics expression for the entropy of a thermodynamic system, the weighting applied to said statistical-mechanics expression being the number of different words associated with each of said signal segments.

9. The signal receiver of claim 2 wherein said thermodynamics-related quantities are obtained from a weighted statistical-mechanics expression for the energy of a thermodynamic system, the weighting applied to said statistical-mechanics expression being the number of different words associated with each of said signal segments.

10. The signal receiver of claim 2 wherein said thermodynamics-related quantities are obtained from a weighted statistical-mechanics expression for the specific heat capacity of a thermodynamic system, the weighting applied to said statistical-mechanics expression being the number of different words associated with each of said signal segments.

11. The signal receiver of claim 2 further comprising a receiver front end which generates inphase and quadrature components of said electrical signal, the input to said ADC being said inphase and quadrature components, the output of said ADC being inphase and quadrature word sequences, the operations performed by said digital processor further comprising the combining of said inphase and quadrature word sequences into a combination word sequence, said combination word sequence being the subject of the operations performed by said digital processor in transforming said word sequences into said thermodynamics-related quantities.

12. The signal receiver of claim 11 wherein said combination word sequence is obtained by selecting the larger of corresponding inphase and quadrature words.

13. The signal receiver of claim 11 wherein said combination word sequence is obtained by summing the absolute values of corresponding inphase and quadrature words.

14. The signal receiver of claim 11 wherein said combination word sequence is obtained by taking the square root of the sum of the squares of corresponding inphase and quadrature words.

15. The signal receiver of claim 1 wherein said electrical signal is comprised of a plurality of delayed and attenuated replicas of a periodic transmitted signal, the operations performed by said digital processor further comprising the averaging of a plurality of said signal segments to obtain an average signal segment, the beginnings of said signal segments being separated in time by an integral number of periods of said transmitted signal, the average signal segment being the subject of operations performed by said digital processor in calculating said thermodynamics-related quantities.

16. The signal receiver of claim 1 wherein each of said signal segments has an origin, said signal receiver further comprising a display device which displays the magnitudes of said thermodynamics-related quantities as a function of origin.

17. The signal receiver of claim 1 wherein each of said signal segments is associated with a propagation time, said signal receiver further comprising a display device which displays the magnitudes of said thermodynamics-related quantities as a function of propagation time.

18. A system for detecting sand characterizing wave emitter intensity and objects, discontinuities, and other inhomogeneities in a wave-propagating medium, said system comprising:

a wave-sensing means for converting waves received at said wave-sensing means through a predetermined solid angle into a received electrical signal;

a receiver which transforms each of a plurality of time segments of said received signal into a thermodynamics-related quantity;

a display means for displaying the magnitudes of said thermodynamics-related quantities as a function of signal segment origin, the origin of said signal segments being determined from said predetermined solid angle, the changes in said thermodynamics-related quantities corresponding to variations in the wave emitter intensity and to objects, discontinuities, and other inhomogeneities in the wave-propagating medium.

19. A probing system for detecting and characterizing objects, discontinuities, and other inhomogeneities in a wave-propagating medium, said probing system comprising:

a transmitter for generating an electrical signal;

a wave-generating means for converting said transmitter signal into transmitted waves propagated through a first solid angle in said wave-propagating medium;

a wave-sensing means for converting waves received at said wave-sensing means through a second solid angle into a received electrical signal, said received waves arising as a result of said transmitted waves being reflected or scattered by objects, discontinuities, and other inhomogeneities in said propagation medium;

a receiver which transforms each of a plurality of time segments of said received signal into a thermodynamics-related quantity;

a display means for displaying the magnitude of said thermodynamics-related quantity as a function of signal segment origin, the origins of said signal segments being determined from said first and second solid angles and the time required to propagate said signal segments from said transmitter to said receiver, the changes in said thermodynamics-related quantities corresponding to objects, discontinuities, and other inhomogeneities in said wave-propagating medium.

20. A method for detecting changes in structure and level of a signal as a function of time comprising the steps:
dividing said signal into time segments;
transforming each of said signal segments into a thermodynamics-related quantity;
displaying said thermodynamics-related quantities for purposes of comparison, the differences in said thermodynamics-related quantities corresponding to changes in said signal structure and/or level.

21. The method of claim 20 wherein said thermodynamics-related quantities are obtained in said transforming step from a statistical-mechanics expression for the sum-over-states of a thermodynamic system.

22. The method of claim 20 wherein said thermodynamics-related quantities are obtained in said transforming step from a statistical-mechanics expression for the entropy of a thermodynamic system.

23. The method of claim 20 wherein said thermodynamics-related quantities are obtained in said transforming step from a statistical-mechanics expression for the energy of a thermodynamic system.

24. The method of claim 20 wherein said thermodynamics-related quantities are obtained in said transforming step from a statistical-mechanics expression for the specific heat capacity of a thermodynamic system.

25. The method of claim 20 wherein said thermodynamics-related quantities are obtained in said transforming step from a weighted statistical-mechanics expression for the sum-over-states of a thermodynamic system, the weighting applied to said statistical-mechanics expression being the number of signal levels in each of said signal segments that differ from one another by at least a predetermined increment.

26. The method of claim 20 wherein said thermodynamics-related quantities are obtained in said transforming step from a weighted statistical-mechanics expression for the entropy of a thermodynamic system, the weighting applied to said statistical-mechanics expression being the number of signal levels in each of said signal segments that differ from one another by at least a predetermined increment.

27. The method of claim 20 wherein said thermodynamics-related quantities are obtained from a weighted statistical-mechanics expression for the energy of a thermodynamic system, the weighting applied to said statistical-mechanics expression being the number of signal levels in each of said signal segments that differ from one another by at least a predetermined increment.

28. The method of claim 20 wherein said thermodynamics-related quantities are obtained from a weighted statistical-mechanics expression for the specific heat capacity of a thermodynamic system, the weighting applied to said statistical-mechanics expression being the number of signal levels in each of said signal segments that differ from one another by at least a predetermined increment.

29. A signal receiver for practicing the method of claim 20.

30. A method for detecting and characterizing wave emitter intensity and objects, discontinuities, and other inhomogeneities in a wave-propagating medium comprising the steps:
converting waves arriving at a receiving point through a predetermined solid angle into a received electrical signal;
dividing said electrical signal into time segments;
transforming each of said signal segments into a thermodynamics-related quantity;
determining the origin of each of said signal segments from said predetermined solid angle;
displaying the magnitude of each of said thermodynamics-related quantities as a function of origin;
interpreting changes in thermodynamics-related quantities in terms of variations in wave emitter intensity and objects discontinuities, and other inhomogeneities in the wave-propagating medium.

31. A system for practicing the method of claim 30.

32. A method for detecting and characterizing objects, discontinuities, and other inhomogeneities in a wave-propagating medium comprising the steps:
propagating waves form a transmitting point through a first solid angle in said wave-propagating medium;
converting waves arriving at a receiving point through a second solid angle into an electrical signal, said arriving waves arising as a result of reflection or scattering of said propagated waves by objects, discontinuities, and other inhomogeneities in said wave-propagating medium;
dividing said electrical signal into time segments;
transforming each of said signal segments into a thermodynamics-related quantity;
determining the mean propagation time between said transmitting and receiving points for each of said signal segments;
determining the origin of each of said signal segments from said first and second solid angles and said mean propagation time;
displaying the magnitude of each of said thermodynamics-related quantities as a function of origin;
interpreting changes in said thermodynamics-related quantities in terms of objects, discontinuities, and other inhomogeneities in said wave-propagating medium.

33. A probing system for practicing the method of claim 32.

34. A method of using the system of claim 18 to detect variations in intensity of an electromagnetic emitter radiating from a point in space at a known frequency, said method comprising the steps:
selecting a wave-sensing means that responds to electromagnetic waves at the emitter frequency;
orienting said wave-sensing means so that emitter is within said receiving solid angle of said wave-sensing means;
observing the display of said thermodynamics-related quantity over time.

35. A method of using the system of claim 18 to detect wave emitters in a region of space, said region of space subtending a solid angle at said probing system that is larger than said predetermined receiving solid angle of said wave-sensing means, said method comprising operations (A) and (B) performed simultaneously:
(A) operating equipment;
(a) identifying N orientations of said wave-sensing means such that every portion of said region-of-space solid angle is within at least one of said N receiving solid angles;
(b) placing said wave-sensing means in the n'th orientation;
(c) operating said probing system for a predetermined time period;
(d) setting $n = n_{modulo\ N} + 1$;
(e) repeating steps (b) through (e);

B. interpreting localized changes in the thermodynamics-related quantities displayed on said display means as emitters.

36. A method of using the probing system of claim 19 to detect objects, discontinuities, and other inhomogeneities in a region of space, said wave-generating means and said wave-sensing means being a single device called a wave-converting means, said first and second solid angles being substantially coincident, said region of space subtending a solid angle at said probing system that is larger than said first and second solid angles, said method comprising operations (A) and (B) performed simultaneously:

(A) operating equipment;
  (a) identifying N orientations of said wave-converting means such that every portion of said region-of-space solid angle is within at least one of said N transmitting/receiving solid angles;
  (b) placing said wave-converting means in the n'th orientation;
  (c) operating said probing system for a predetermined time period;
  (d) setting $n = n_{modulo\ N} + 1$;
  (e) repeating steps (b) through (e);
B. interpreting localized changes in the thermodynamics-related quantities displayed on said display means as objects, discontinuities, or other inhomogeneities in said wave-propagating medium.

37. A method of using the probing system of claim 19 to detect objects, discontinuities, and other inhomogeneities in a region of space, said region of space subtending solid angles at said wave-generating means and at said wave-sensing means that are larger than said first and second solid angles, said method comprising operations (A) and (B) performed simultaneously:

(A) operating equipment;
  (a) identifying N orientations of said wave-generating means and M orientations of said wave-sensing means such that every portion of said region-of-space solid angle subtended by said wave-generating means is within at least one of said N first solid angles and such that every portion of said region-of-space solid angle subtended by said wave-sensing means is within at least one of said M second solid angles;
  (b) placing said wave-generating means in the n'th orientation and said wave-sensing means in the m'th orientation;
  (c) operating said probing system for a predetermined time period;
  (d) setting $m = m_{modulo\ M} + 1$;
  (e) setting $n = n_{modulo\ N} + 1$ if $m = 1$;
  (f) repeating steps (b) through (f);
B. interpreting localized changes in the thermodynamics-related quantities displayed on said display means as objects, discontinuities, or other inhomogeneities in the wave-propagating medium.

* * * * *